United States Patent
Okada

(10) Patent No.: US 7,534,621 B2
(45) Date of Patent: May 19, 2009

(54) METHOD OF PRODUCING PROBE MEDIUM AND METHOD OF IMMOBILIZING PROBE USING PROBE MEDIUM

(75) Inventor: Yoshikatsu Okada, Kanagawa (JP)

(73) Assignee: Canon Kabuhsiki Kashia, Tokyo (JP)

( * ) Notice: Subject to any disclaimer, the term of this patent is extended or adjusted under 35 U.S.C. 154(b) by 732 days.

(21) Appl. No.: 10/770,458

(22) Filed: Feb. 4, 2004

(65) Prior Publication Data
US 2004/0203040 A1 Oct. 14, 2004

(30) Foreign Application Priority Data
Feb. 7, 2003 (JP) ............................. 2003-031670

(51) Int. Cl.
*G01N 33/00* (2006.01)
*C12M 1/34* (2006.01)
*C07H 21/04* (2006.01)

(52) U.S. Cl. .................... 436/94; 435/287.2; 536/23.1; 536/24.3

(58) Field of Classification Search .................. 436/94; 435/287.2; 536/23.1, 24.3
See application file for complete search history.

(56) References Cited

U.S. PATENT DOCUMENTS

| 4,139,346 A | * | 2/1979 | Rabbani | 422/56 |
| 5,010,183 A | * | 4/1991 | Macfarlane | 536/25.4 |
| 5,741,638 A | | 4/1998 | Yamane | 435/6 |
| 5,874,219 A | | 2/1999 | Rava et al. | 435/6 |
| 6,017,742 A | | 1/2000 | Takenishi et al. | 435/180 |
| 6,476,215 B1 | | 11/2002 | Okamoto et al. | 526/25.3 |
| 2001/0055762 A1 | | 12/2001 | Suzuki et al. | 435/6 |
| 2002/0006623 A1 | * | 1/2002 | Bradley et al. | 435/6 |
| 2004/0005620 A1 | | 1/2004 | Okada et al. | 435/6 |

FOREIGN PATENT DOCUMENTS

| JP | 5192198 | | 8/1993 |
| JP | 8023975 | | 1/1996 |
| JP | 2794728 | | 6/1998 |
| JP | 2000-146971 | | 5/2000 |
| WO | WO 00/65097 | * | 11/2000 |
| WO | 01/46214 | | 6/2001 |

OTHER PUBLICATIONS

T. Okamoto, et al., "Microarray fabrication with covalent attachment of DNA using Bubble Jet technology", Nature Biotechnology, vol. 18, No. 4, pp. 438 to 441 (2000).
M. Pirrung, "How to Make a DNA Chip", Angew. Chem. Int. Ed., vol. 41, No. 8, pp. 1277 to 1289 (2002).
Official Action dated Jan. 12, 2009 in European Application No. 04002557.9.

* cited by examiner

*Primary Examiner*—Bradley L Sisson
(74) *Attorney, Agent, or Firm*—Fitzpatrick, Cella, Harper & Scinto

(57) ABSTRACT

When a probe medium is spotted on a substrate, a probe can be effectively and stably immobilized on the substrate. The probe medium includes a probe capable of specifically binding to a target substance, a medium containing an organic solvent, and a substance for solubilizing the probe in the organic solvent.

3 Claims, No Drawings

SEQUENCE LISTING

```
<160> NUMBER OF SEQ ID NOS: 1

<210> SEQ ID NO 1
<211> LENGTH: 18
<212> TYPE: DNA
<213> ORGANISM: Artificial
<220> FEATURE:
<223> OTHER INFORMATION: DNA probe

<400> SEQUENCE: 1
actggccgtc gttttaca                                          18
```

METHOD OF PRODUCING PROBE MEDIUM AND METHOD OF IMMOBILIZING PROBE USING PROBE MEDIUM

BACKGROUND OF THE INVENTION

1. Field of the Invention

The present invention relates to a probe medium that includes a probe capable of specifically binding to a target substance and a method of producing the probe medium. In addition, the present invention relates to a probe medium useful for effectively immobilizing a probe on a substrate, a method of producing the probe medium, and a method of immobilizing a probe using the probe medium. Furthermore, the present invention relates to a probe-immobilized substrate obtained by immobilizing a probe on a substrate, and a detection element and a detection method for detecting a target substance using the probe-immobilized substrate.

2. Related Background Art

Recent advances in the field of biotechnology including genetic engineering and molecular biology have made possible diagnostics of infectious diseases, cancers, genetic disorders, and so on in DNA and RNA levels. As one of tools used for the diagnosis with nucleic acids such as DNA or RNA, attentions have been focused on DNA chips and DNA arrays. In the diagnostic tools including DNA chips and DNA arrays, probes such as nucleic acids are immobilized on a substrate and then the probes are hybridized with their target substances to detect those target substances. The probes capable of specifically binding to the target substances such as DNA, RNA, and nucleic acids are soluble in water and thus they can be easily dissolved in water, but hardly soluble in organic solvents such as ethyl alcohol, isopropyl alcohol, isoamyl alcohol, dipropylene glycol, and chloroform.

For the formation of a substrate on which a probe such as a DNA chip or a DNA array prepared in advance is immobilized by a spotting method or the like, conventionally a probe medium is prepared by dissolving the probe in an aqueous solution containing water or a mixture of water and a pH-adjusting material when the probe is immobilized on the substrate, and the probe medium is contacted with the substrate to immobilize the probe on the substrate. More specifically, for example, Japanese Patent Application Laid-Open No. H08-23975 describes a method of immobilizing a probe on a substrate, in which a probe aqueous solution is prepared by dissolving DNA in water and the probe medium thus prepared is dispensed and dropped into a surface-treated well-plate to immobilize the probe on the substrate. In addition, Japanese Patent Application Laid-Open No. H05-192198 describes a method of preparing a probe medium by adjusting the concentration of DNA by dissolving the DNA in a 10-mM Tris-HCl (pH 7.6)/1-mM EDTA solution, adding four-fold volumes of $H_2O$ and five-fold volumes of an immobilization buffer (1.5 M NaCl, 0.3 M Tris-HCl (pH 8.0), and 0.3 M $MgCl_2$) to the DNA in buffer, and mixing them together. In Japanese Patent Application Laid-Open No. 2000-146971, furthermore, there is described a method in which an aqueous solution of oligonucleotide biotin-introduced to 5'-end is prepared, dotted on an isocyanated slide glass, and immobilized in an incubator at 37° C. for 15 minutes. Moreover, in Japanese Patent No. 2794728, a single-stranded DNA is serially diluted with a TE buffer (10 mM Tris-HCl (pH 7.5)/1 mM EDTA) to prepare a probe medium. The prepared probe medium was dotted on a nitrocellulose film, followed by air- and heat-drying to immobilize the DNA on a substrate.

However, among probe media including probes that are conventionally used and capable of specifically binding to the respective target substances, as a medium for immobilizing a probe on a substrate, there is no probe medium in which the probe is dissolved in an organic solvent where the probe is insoluble. Among those, furthermore, there is no probe medium containing a substance capable of solubilizing a probe in an organic solvent where the probe is insoluble. In each of the probe media conventionally used, a probe capable of specifically binding to a target substance is dissolved in water or an aqueous solution that contains water, a pH-adjusting substance, and an adsorption-lowering substance. Furthermore, it is also known that the addition of a small amount of a glycol-based solvent or an alcohol-based solvent is preferable to dot the probe medium on a substrate by spotting or the like. However, there is no probe medium prepared such that a probe such as nucleic acids of DNA or RNA is dissolved in a probe-insoluble organic solvent. Therefore, because of insolubility of the probe in an organic solvent, it has been difficult to realize a probe medium only including an organic solvent without containing water even though it is suitable to preferably dot the probe medium on the substrate.

Dissolving a probe such as nucleic acids of DNA or RNA in an organic solvent is known to extract the probe from a sample. However, as a probe medium to be used for immobilizing the probe on a substrate, no probe medium in which a probe is dissolved in an organic solvent has been known. In addition, for binding a probe such as nucleic acids of DNA or RNA to a carrier capable of binding to nucleic acids, the carrier suspended in a solution containing a surfactant is used to bind the nucleic acids for the extraction thereof. However, there is no case in which a probe is dissolved in a solution containing a surfactant and then the resultant solution is used as a probe medium.

SUMMARY OF THE INVENTION

A first object of the present invention is to provide a probe medium comprising: a probe capable of specifically binding to a target substance, an organic solvent, and a substance for solubilizing the probe in an organic solvent.

A second object of the present invention is to dissolve a probe in a solvent in which the probe is soluble and acting the solvent on a substance for solubilizing the probe in an organic solvent to separate the probe from the solvent, and adding the organic solvent to the probe to dissolve the probe therein.

A third object of the present invention is to confirm the amount of a substance for solubilizing a probe in an organic solvent from the precipitation and redissolution of the probe and prepare the amount of the substance so as to precipitate the probe, thereby effectively dissolving the probe in the organic solvent.

The above-mentioned problems have been solved by the present invention described below. That is, the present invention includes the following configurations:

(1) A probe medium comprises: a probe capable of specifically binding to a target substance; a medium containing an organic solvent; and a substance for solubilizing the probe in the organic solvent. The probe is preferably a nucleic acid probe. The organic solvent is preferably a solvent in which the probe is insoluble. The substance for solubilizing the probe in the organic solvent is preferably an amphipathic substance. The substance for solubilizing the probe in the organic solvent is preferably a substance selected from the group consisting of n-hexadecyl trimethyl ammonium bromide, n-hexadecyl trimethyl ammonium chloride, and cetylpyridinium chloride, or a mixture containing at least a substance selected from the group. Preferably, the probe medium further comprises a substance for immobilizing the probe on a substrate. The substance for immobilizing the probe on the substrate is preferably a silane coupling agent. Preferably, the probe medium further comprises a solvent in which the probe is soluble. An amount of the substance for solubilizing the probe in the organic solvent is preferably adjusted within a range in which white turbidity of the probe medium can be observed.

(2) A method of producing a probe medium that contains a probe capable of specifically binding to a target substance, comprises the steps of: dissolving the probe in a solvent in which the probe is soluble; separating the probe from the solvent by acting on the solvent a substance for solubilizing the probe in the organic solvent; and dissolving the probe in an organic solvent by adding the organic solvent to the probe. An amount of the substance for solubilizing the probe in the organic solvent is preferably acted on the basis of a product between a length of the probe and a mole number of the probe. An amount of the substance for solubilizing the probe in the organic solvent is preferably acted on the basis of an amount of the probe separated from the solvent.

(3) A method of immobilizing a probe on a substrate by providing a probe medium on the substrate by spotting.

(4) A detection element produced by the probe-immobilizing method.

According to the present invention, a probe can be effectively immobilized on a substrate by use of a probe medium including a probe capable of specifically binding to a target substance, a medium containing an organic solvent, and a substance for solubilizing the probe in the organic solvent. The probe medium includes the probe and the substance for solubilizing the probe in the organic solvent to allow the probe to be dissolved in the organic solvent, so that the probe medium can be prepared as one having a suitable composition for spotting the probe medium on the substrate. In addition, when the probe medium contains a substance for immobilizing the probe on the substrate, the probe can be effectively bound to the substance for immobilizing the probe, allowing the probe to be efficiently immobilized on the substrate. Furthermore, by binding between the probe and the substance for immobilizing the probe on the substrate, the control of the production process can be simplified and the production time can be shortened.

According to the present invention, furthermore, for immobilizing different probes on a substrate, it is possible to select any kind of the binding substance and the concentration thereof on the basis of each probe type. Besides, it is possible to suitably select a probe-immobilizing substance depending on the probe type. Moreover, it is possible to prepare the composition of the probe medium depending on the probe and the substance for immobilizing the probe on the substrate. Therefore, many different probes can be bound to one substrate under the most favorable conditions for every combination of the probe type and the probe-immobilizing substance.

Furthermore, after dissolving the probe in the probe-soluble solvent, a substance for solubilizing the probe in the organic solvent acts on the solvent to separate the probe from the solvent and an organic solvent is added to the probe to dissolve the probe in the organic solvent, thereby effectively immobilizing the probe on the substrate.

DESCRIPTION OF THE PREFERRED EMBODIMENTS

A probe medium according to the present invention comprises a probe capable of specifically binding to a target substance, a medium containing an organic solvent, and a substance for solubilizing the probe in the organic solvent. In addition, the probe medium of the present invention is produced by a method comprising the steps of dissolving a probe in a probe-soluble solvent, acting the probe on a substance for solubilizing the probe in an organic solvent to separate the probe from the solvent, and adding an organic solvent in which the probe is insoluble to the probe to dissolve the probe in the organic solvent. According to the present invention, the method of producing the probe medium which comprises the above-mentioned steps. Furthermore, according to the present invention, a method of immobilizing a probe on a substrate comprises the step of allowing the probe medium to adhere on the substrate.

The probes include single-stranded nucleic acid probes, single-stranded DNA probes, single-stranded RNA probes, single-stranded PNA probes, and single sugar chain probes. Considering the stability of the probe in the probe medium, for example, the probe medium is prepared such that the content of the probe of 2 mer to 500 mer, particularly of 2 mer to 80 mer is in the range of 0.05 to 500 µmol/liter (hereinafter, "liter" is abbreviated to "l"), particularly in the range of 0.5 to 50 µmol/l.

Those probes may have reaction sites for binding to the substrate. The reaction site may be a functional group, biotin, or the like and may be provided as a part of a linker having an appropriate length. For instance, the functional groups include an amino ($NH_2$) group, a carbonyl (COOH) group, a mercapto (SH) group, and a hydroxyl (OH) group. In particular, the probe functional group is preferably an amino group in consideration of the easiness in the synthesis of the probe functional group or a mercapto group in consideration of the reactivity of the probe functional group.

The solvents in which probes are soluble include water, ethylene glycol, and propylene glycol. In addition, as needed, two or more of those solvents may be used in combination with each other. The water may be one in a probe-dissolving solution to which a salt such as sodium chloride or an acid such as phosphoric acid is added.

The substances for solubilizing the probes in the organic solvents may be preferably of amphipathic and specifically include surfactants, surfactants capable of forming micelle catalysts, and the like. Among those, particularly preferable surfactants are cationic surfactants including cetylpyridinium chloride, cetyltrimethylammonium bromide, and cetyltrimethylammonium chloride. Considering the stability of the probe, and the solubility of the probe to the organic solvent, the content of the surfactant in the probe medium is adjusted so as to be, for example, 0.2 µmol/l or more, preferably 1 µmol/l or more, but 400,000 µmol/l or less, preferably 40,000 µmol/l or less. The amount of the surfactant to act on the probe medium is adjusted on the basis of the product of the length of the probe and the mole number of the probe. The amount of the surfactant to act on the probe medium is also adjusted on the basis of the amount of the probe separated from the solvent. Furthermore, the amount of the surfactant to act on the probe medium is confirmed by checking precipitation or re-dissolution of the probe and then adjusted such that the probe can be precipitated. Moreover, the inventors of the present invention have found out that the content of the surfactant is preferably adjusted within the range in which the probe medium causes a white turbid suspension.

The probe-insoluble organic solvents include not only alcohols and ketones but also many other organic solvents such as those capable of immobilizing probes (e.g., silane coupling agents) on the substrate. In addition, the organic solvent in the probe medium may be of a single type or a mixture of two or more types. When the probe is bound to the substrate without the interposition of other substance, i.e., without containing the organic solvent for immobilizing the probe on the substrate in the probe-insoluble organic solvent, the probe-insoluble organic solvent is preferably one of solvents such as alcohols having no reaction site with the probe and the substrate. Alternatively, the probe-insoluble organic solvents may include organic solvents capable of immobilizing the probe on the substrate through the reaction between the probe and the substrate. In particular, when the probe is not bound to the substrate or hardly bound to the substrate, it is preferable that the probe-insoluble organic solvent contains an organic solvent for immobilizing the probe on the substrate. As the organic solvent for immobilizing the probe on the substrate, a solvent having reaction sites with the probe and substrate may be a silane coupling agent or the like. There are various silane coupling agents known, preferably, which include an epoxy silane coupling agent, isocyanate silane coupling agent, mercapto silane coupling agent, chloropropyl silane coupling agent, and amino silane coupling agent. In consideration of the immobilizing property of the probe to the substrate, the content of the organic solvent for immobilizing the probe in the medium on the substrate is preferably adjusted to, for example, 0.05 to 50,000 µmol/l, particularly 10 to 500 µmol/l in the probe medium. The reaction between the probe functional group and the organic solvent is preferably of a covalent bond between the functional groups as a result of their chemical reaction. In the chemical reaction, when the functional group of the probe is an amino ($NH_2$) group, preferable organic solvents include an epoxy silane coupling agent, an isocyanate silane coupling agent, a mercapto silane coupling agent, and a chloropropyl silane coupling agent. When the functional group of the, probe is a carbonyl (COOH) group, preferable organic solvents include an amino silane coupling agent and a mercapto silane coupling agent. When the functional group of the probe is a mercapto (SH) group, preferable organic solvents include an epoxy silane coupling agent, an isocyanate silane coupling agent, and a vinyl silane coupling agent. The alcohols include ethanol, 1-propanol, 1-butanol, and 2-butanol. Ketones include acetone and methylethyl ketone. Amino silane coupling agents include γ-aminopropyl trimethoxy silane, and N-β (aminoethyl) γ-aminopropyl trimethoxy silane. Epoxy silane coupling agents include γ-glycidoxypropyl trimethoxy silane, and γ-glycidoxypropyl triethoxy silane. Isocyanate silane coupling agents include γ-isocyanate propyl triethoxy silane, and γ-isocyanate propyl trimethoxy silane. Mercapto silane coupling agents include γ-mercapto propyl trimethoxy silane. Chloropropyl silane coupling agents include γ-chloropropyl trimethoxy silane. Vinyl silane coupling agents include vinyl trimethoxy silane. The probe-insoluble organic solvent may be a mixture solvent of those organic solvents. The probe-insoluble organic solvent is preferably an organic solvent prepared by mixing a probe, a probe-soluble solvent, a substance for solubilizing the probe in the organic solvent, and a probe-insoluble organic solvent such that no separation into two or more phases occurs at the time of preparing a probe medium, or a mixture solvent of organic solvents.

Furthermore, the probe medium may be mixed with a water-soluble polymer material as needed. The water-soluble polymer materials include polyvinyl alcohol (PVA), polyvinyl pyrrolidone (PVP), paogen, carboxymethyl cellulose (CMC), hydroxyethyl cellulose (HEC), dextran, and pullulan. Preferable water-soluble polymer materials are those generally used, such as polyvinyl alcohol (PVA) and polyvinyl pyrrolidone (PVP). Those polymer materials may be used alone or in combination with each other if required.

A preferable method of mixing the water-soluble polymer material into the medium includes the steps of preparing a solution with a predetermined concentration of a water-soluble polymer material completely dissolved therein in advance, weighing out the resultant polymer material solution so as to obtain a predetermined concentration of the polymer material solution in the medium, and mixing the weighed polymer solution into the medium. Specific examples of the polymer material solution include one obtained by weighing out an appropriate amount of polyvinyl alcohol powder and adding the powder to pure water so as to be 0.5 to 5% by mass in concentration, followed by dissolving the powder in the water under heat. Preferably, the resultant polymer aqueous solution is mixed into the probe medium such that its content in probe medium is 0.01 to 1% by mass.

There are several procedures for producing the probe medium.

Different procedures are selected depending on whether the probe-insoluble organic solvent contains the organic solvent for immobilizing the probe on the substrate.

When the probe-insoluble organic solvent contains the organic solvent for immobilizing the probe on the substrate, the following process can be used as a first process. At first, the probe is mixed with a small amount of a probe-soluble solvent to dissolve the probe in the solvent. Then, a substance for solubilizing the probe in the organic solvent is added to the probe-dissolved solvent. The processes for the addition of the substance include a process of mixing the substance into the probe-dissolved solvent, a process of dissolving the substance in the probe-soluble solvent so as to have a predetermined concentration thereof before the mixing, and a process of dissolving the substance in the probe-insoluble organic solvent so as to have a predetermined concentration thereof before the mixing. Among those, preferable is the process of dissolving the substance in the probe-soluble solvent before the mixing from the viewpoint of effective mixing. In the probe-soluble solvent, the concentration of the substance for solubilizing the probe in the organic solvent is preferably as high as possible in terms of effectively dissolving the probe in the organic solvent. The solution containing the substance for solubilizing the probe in the organic solvent is dropped into the probe-dissolved solvent and mixed therewith. The amount of the substance dropped is suitably set such that the mole number of the substance for solubilizing the probe in the organic solvent corresponds to the result of multiplying the product of the mole number of the probe and the chain length of the probe by 0.2 to 4, preferably by 0.5 to 3. The probe can be separated from the solvent by adding the substance for solubilizing the probe in the organic solvent to the probe-dissolved solvent. Furthermore, the probes separated may be accumulated with precipitation by centrifugation. The organic solvent for immobilizing the probe on the substrate is dropped and mixed into the solvent containing the separated probe. The mixing amount of the organic solvent is suitably adjusted to have the mole number moles 0.5 to 500 times, preferably 1.0 to 50 times as large as the mole number of the probe, although the amount varies depending on the probe functional group or the organic solvent for immobilizing the probe on the substrate. Further, considering an immobilizing property on the substrate of the probe, its content in the probe medium is preferably adjusted to 0.05 to 50,000 µmol/l, more preferably, 10 to 500 µmol/l, for instance. The mixing method is not specifically limited as far as it is a method of mixing the probe separated by the addition of the substance for solubilizing the probe in the organic solvent and the organic solvent for immobilizing the probe on the substrate. When the specific gravity of the organic solvent for immobilizing the probe on the substrate is higher than that of the probe-soluble solvent, an effective reaction can be attained by gently dropping the probe-immobilizing organic solvent into the solvent containing the probe in the separated and precipitated form and centrifuging the resultant mixture for the precipitation. If required, it may be heated. When heating, a temperature may be raised to 40° C. to 80° C. When the specific gravity of the organic solvent for immobilizing the probe on the substrate is smaller than that of the probe-soluble solvent, the probe should be sufficiently separated from the solvent and precipitated in a vessel to immobilize the probe on the bottom thereof, followed by gently dropping the probe-immobilizing organic solvent onto the probe-containing solvent. Subsequently, the vessel is sealed and then slanted or the contents thereof are stirred to react them with each other. Just as in the case of large specific gravity, it may be heated up if required. After mixing with the organic solvent for immobilizing the probe on the substrate, if it is preferable to prepare the resultant mixture as a single-phase probe medium, the addition of an organic solvent may realize such a single phase. For instance, when the organic solvent for immobilizing the probe on the substrate is an isocyanate silane coupling agent and the probe-soluble solvent is water, the single phase can be obtained by the addition of 2-propanol or dipropylene glycol. As far as no trouble is found in immobilization of the probe on the substrate, the single phase is preferable in terms of treating the probe medium. The amount of such an organic solvent added is, although not specifically limited to, preferably within the range suitable for setting a predetermined concentration of the probe and immobilizing the probe on the substrate as far as the formation of the single phase is allowed. Furthermore, when needed, the water-soluble polymer and water may be mixed. As a method of mixing the water-soluble polymer and water, it is preferable that an aqueous solution of the water-soluble polymer is prepared and then dropped and mixed so as to reach a predetermined amount.

As a second process, the following process can be used. At first, a solution prepared by dissolving the substance for solubilizing the probe in the organic solvent in the probe-soluble solvent is dropped and mixed into a probe-containing vessel. Then, the probe turns soluble in the organic solvent, while it turns insoluble in the probe-soluble medium. As a result, the probe is precipitated. Subsequently, the organic solvent for immobilizing the probe on the substrate is dropped into the vessel and then mixed well. For a sufficient coupling between the probe and the organic solvent for immobilizing the probe on the substrate, it is preferable to adjust the time and temperature of the mixing. For the mixing of the organic solvent, the mixing of the water-soluble polymer and the mixing of water, the same procedure as that of the first process may be performed.

A third process is to mix the probe and the substance for solubilizing the probe in the organic solvent in advance. After dissolving the probe with a small amount of the probe-soluble solvent, a solution prepared by dissolving the substance for solubilizing the probe in the organic solvent in the probe-soluble solvent is dropped and mixed into the probe-dissolved solvent. After confirming that the probe turns insoluble and precipitates, the mixture is dried up to remove the excess solvent. As a result, the residue in the vessel is the product of mixing the probe and the substance for solubilizing the probe in the organic solvent. As the residue can be dissolved in any organic solvent, the probe is dropped and mixed into the organic solvent for immobilizing the probe on the substrate. For allowing the probe to be sufficiently coupled with the substance for immobilizing the probe on the substrate, it is preferable to adjust the time and temperature of the mixing. For the mixing of the organic solvent, the mixing of the water-soluble polymer and the mixing of water, the same procedure as that of the first process may be performed. The medium prepared by mixing the probe and the substance for solubilizing the probe in the organic solvent as used in this method can be provided as a probe-immobilizing reagent.

When the probe-insoluble organic solvent does not contain the organic solvent for immobilizing the probe on the substrate, the first process may take the following steps. At first, just as in the case of containing the organic solvent for immobilizing the probe on the substrate, the probe, the probe-soluble solvent, the substance for solubilizing the probe in the organic solvent are mixed together, and then the probe is separated from the solvent. Subsequently, the probe-insoluble organic solvent is dropped and mixed into the solvent that contains the separated probe. The separated probe is dissolved into the probe-insoluble organic solvent to provide a probe medium as a mixture medium composed of the organic solvent and the probe-soluble medium. When the mixture medium composed of the organic solvent and the probe-soluble medium is not formed of a single phase, an additional organic solvent may be mixed into the mixture medium to turn the probe medium into a single-phase medium. As far as no trouble is found in immobilization of the probe on the substrate, the single-phase probe medium is preferable in terms of treating the probe medium. Furthermore, when needed, the water-soluble polymer and water may be mixed therein. As a method of mixing the water-soluble polymer and water, it is preferable that an aqueous solution of the water-soluble polymer is prepared and then dropped and mixed so as to reach a predetermined amount.

As a second process, the following process can be used. At first, a solution prepared by dissolving the substance for solubilizing the probe in the organic solvent in the probe-soluble solvent is dropped into a probe-containing vessel and they are mixed. Then, the probe is dissolved in the organic solvent. As a result, the probe is precipitated. Subsequently, the organic solvent is dropped and then mixed to dissolve the probe therein. The organic solvent may be mixed as in the first process. The mixing of the water-soluble polymer and the mixing of water may be carried out as in the case of the first process.

A third process is to mix the probe and the substance for solubilizing the probe in the organic solvent in advance. After dissolving the probe with a small amount of the probe-soluble solvent, an aqueous solution prepared by dissolving the substance for solubilizing the probe in the organic solvent in the probe-soluble solvent is dropped and mixed thereinto. After confirming that the probe turns insoluble and precipitates, the mixture is dried up to remove the excess solvent. As a result, the residue in the vessel is the product of mixing the probe and the substance for solubilizing the probe in the organic solvent. As the residue can be dissolved in an organic solvent, the organic solvent for immobilizing the probe on the substrate is dropped and mixed to dissolve the probe thereinto. For the mixing of the organic solvent, the same procedure as that of the first process may be performed. Further, the mixing of the water-soluble polymer and the mixing of water may be performed as in the first process.

The probe medium thus obtained is suitable as a probe medium to be used for preparing an immobilized probe for the detection of a target substance.

A probe-immobilized substrate can be prepared by spotting the obtained probe medium on a substrate. The substrate for immobilizing the probe thereon is, although not specifically limited to, preferably a glass or quartz substrate material, a resin substrate, a plastic substrate, or a resin film in consideration of the detection of a target substance and its general-purpose applications. In particular, a preferable material is a slide glass of 1×3 inches in size. In consideration of the immobilizing properties of probe immobilization or the like, when the probe medium contains the organic solvent for immobilizing the probe on the substrate, the substrate is preferably a slide glass substrate made of a no-alkali glass material which is free of an alkali component or the like, or a substrate made of a quartz glass material, a silica-coated glass material, or a silica-coated resin material. When the probe medium does not contain the organic solvent for immobilizing the probe on the substrate, the substrate is preferably a surface-treated glass substrate or resin material substrate. Preferable surface treatment allows the probe to be easily immobilized on the substrate. Specifically, the preferable surface treatment employs a coupling agent or the like to form on the substrate surface a functional group that forms a covalent bond with the probe.

In addition, even though the shape of the substrate is not limited to a plate shape or the like depending on the method of detecting a target substance, the substrate preferably has a plate shape in consideration of the general application of the substrate to the detection methods, apparatuses, and so on. Furthermore, the substrate is desired to have high surface smoothness.

Furthermore, the substrate for immobilizing the probe thereon preferably has a clean surface for uniformly and surely immobilizing the probe. It is desired to ensure a sufficiently cleaned surface by cleaning the substrate before the immobilization of the probe. As a method of cleaning the substrate, there are many known methods. The methods include a method of cleaning a substrate with water, a drug solution, plasma, UV ozone, and air-blowing. Therefore, it is preferable to use one of those cleaning methods with changing a cleaning process and conditions thereof depending on the type of the substrate to be applied.

For instance, when the probe medium contains the organic solvent for immobilizing the probe on the substrate, it is appropriate to clean the surface of the substrate with a drug solution. For example, there is a method of sufficiently cleaning the surface of the substrate with a sodium hydroxide (NaOH) aqueous solution at a predetermined concentration to remove soil attached on the substrate. Specifically, a 1-mol/l NaOH aqueous solution heated at about 50° C. is prepared and then the surface of the substrate is wiped out in the aqueous solution or brushed while showering with the aqueous solution to surely remove the soil attached on the substrate. After the removal of soil, the excess portion of NaOH is washed out with water. Finally, the removal of water content may be performed by $N_2$-blowing. In this manner, the substrate capable of uniformly and surely immobilizing the probe in the probe medium can be obtained.

When the probe medium does not contain the organic solvent for immobilizing the probe on the substrate, it is appropriate that the surface of the substrate is cleaned with water or the solvent, or cleaned with air blowing. For example, there is a method of fully cleaning the surface of the substrate with pure water to remove foreign matter attached on the substrate. Specifically, the removal of foreign matters is attained by showering pure water on the surface of the substrate using a high pressure pure water shower (two-fluid shower). After the removal of foreign matters, the substrate is rinsed again with a shower of pure water to wash out the pure water contaminated with the foreign matters. Finally, the removal of water content may be performed with $N_2$ blowing. In this manner, the substrate capable of uniformly and surely immobilizing the probe in the medium can be obtained.

As a method of spotting the probe in the probe medium on the substrate, there are several known methods. Specifically, a pin method, an injecting method, and a pin and ring method have been known. Among those, the inkjet method is a preferable spotting method because of its ability to exactly spot the medium at a high density.

The spotting method by using inkjet is not specifically limited as far as it satisfies the conditions that the components in the probe medium do not substantially affect the probe, the probe-soluble solvent, the probe-insoluble organic solvent, and the substance for solubilizing the probe in the organic solvent when the probe medium is discharged from an inkjet head as described above, and that the composition of the medium is formulated so as to be normally discharged on the substrate by means of the inkjet head. For instance, when the inkjet head is a bubble jet head having the mechanism of discharging the medium by applying heat energy thereon, a liquid containing glycerin, thiodiglycol, isopropyl alcohol, or acetylene alcohol is preferably a component to be contained in the probe medium. More specifically, a liquid containing 5 to 10% by mass of glycerin, 5 to 10% by mass of thiodiglycol, and 0.5 to 1% by mass of acetylene alcohol is used as a preferable probe medium. Furthermore, when the inkjet head is a piezo inkjet head that discharges the medium using a piezoelectric element, a liquid containing ethylene glycol and isopropyl alcohol is preferably used as a component to be contained in the probe medium. More specifically, a liquid containing 5 to 10% by mass of ethylene glycol and 0.5 to 2% by mass of isopropyl alcohol is used as a preferable probe medium. Among those medium components, the procedure of preparing the probe-soluble medium may be modified if required and the probe-soluble medium may be added before mixing with the water-soluble polymer material.

When the probe medium thus obtained is discharged from the inkjet head and attached on the substrate, the discharged medium forms a spot in the shape of a circle without extending out of the boundary thereof. Similarly, when the probe medium is spotted at a higher density, the connection between the adjacent spots can be effectively prevented. Note that, the characteristics of the probe medium of the present invention are not limited to those described above.

As a method of immobilizing the probe contained in the probe medium applied on the substrate in a predetermined position, surely preventing the probe from being contaminated with the probe in the adjacent spot, and firmly immobilizing the probe on the substrate, there is an effective method of using the organic solvent for immobilizing the probe on the substrate and the substrate each having functional groups which can be reacted with each other or using the probe and the substrate each having functional groups which can be reacted with each other.

As a preferable example, when the probe medium contains the organic solvent for immobilizing the probe on the substrate, there is a combination of a silanol (SiOH) group on the substance for immobilizing the probe on the substrate and a hydroxyl (OH) group on the substrate. Such a combination enables the immobilization of the substance contained in the probe medium applied on the substrate by spotting on the substrate as a result of a reaction between the silanol group of the substance and the hydroxyl group of the substrate. To give a specific example of the substrate, it is preferable that the organic solvent for immobilizing the probe on the substrate includes the silane coupling agent having a silanol group. In addition, it is also preferable that the substrate is the above-mentioned glass substrate, quartz substrate, or resin substrate having the silica-coated surface, each substrate having a hydroxyl group.

When the probe medium does not contain the organic solvent for immobilizing the probe on the substrate, a combination of an amino ($NH_2$) group on the probe and an epoxy group on the substrate, and a combination of an amino ($NH_2$) group on the probe and an isocyanate group on the substrate are preferably exemplified. Such a combination allows the probe to be immobilized on the substrate such that the amino group of the probe in the probe medium applied on the substrate by means of spotting, and the epoxy group or the isocyanate group of the substrate are reacted with each other. Specifically, it is preferable that the probe is DNA attached with an amino group in combination with the substrate having an epoxy group thereon, which is prepared by introducing the epoxy group into a resin substrate surface-treated as described above.

Furthermore, when the probe medium contains the organic solvent for immobilizing the probe on the substrate, it is preferable that the probe and the organic solvent for immobilizing the probe on the substrate are bound together by the reaction between the probe and the substance described above. Such a reaction allows the probe and the organic solvent to tightly bind to each other. As a result, the probe is more firmly immobilized on the substrate, allowing the formation of the probe spot at a predetermined position. In particular, there is prepared a probe medium including a probe having an amino group as a functional group, and a substance having an isocyanate group as a functional group reactive with the probe and a silanol group as a functional group reactive with the functional group of the substrate. Then, a probe solution is prepared by mixing dipropylene glycol, isopropyl alcohol, and so on with the probe medium at a predetermined ratio. When the probe solution is spotted on the substrate having a hydroxyl group as a functional group by use of the inkjet head, the probe solution forms a spot having a predetermined size in a stable manner on the substrate. Therefore, the probe can be immobilized at a predetermined position of the substrate.

Furthermore, when the probe and the organic solvent for immobilizing the probe on the substrate bind to each other through the reaction therebetween, it is preferable to mix polyvinyl alcohol (PVA) as a water-soluble polymer material in the probe medium. More preferably, it is desired to be completely dissolved in advance. Mixing the water-soluble polymer material into the probe medium facilitates the observation on the substrate about the spotting state and also makes the probe medium on the spot after the spotting hard to be dried. As a result, the probe medium and the substrate can be more surely reacted with each other, allowing the probe to be immobilized on the substrate. Furthermore, considering the storage condition of the probe-immobilized substrate formed by the spotting, the above is effective for efficiently and stably detecting the target substance even when the spot of the probe medium formed by the spotting is dried.

It is preferable to dry the substrate on which the probe medium is being spotted. Drying the substrate allows the probe in the probe medium to be surely immobilized on the substrate. As a drying method, various methods including vacuum drying and heat drying can be exemplified. Among those, the heat drying method is suitable because it can be surely carried out in a simple manner. As a heat drying method, preferable is the method of heat drying with a hot plate. In particular, the substrate having the probe medium spotted thereon is left standing on a heated hot plate. After standing for a predetermined period of time, the substrate is taken off the hot plate and then left to cool. Considering a heat resistance of the probe, the hot plate is preferably heated at 100° C. or less. More specifically, the temperature is preferably in the range of 60° C. to 90° C. The standing time of the substrate is preferably 30 minutes or less. More specifically, it is preferably in the range of 1 to 10 minutes.

For instance, a probe medium containing a probe having a base length of 20 mer is prepared in the concentration of the probe of 9 µmol/l. The addition amount of the substance for solubilizing the probe in the organic solvent is adjusted on the basis of the amount calculated by multiplying the amount of the probe by the number of base chains. Preferably, it is prepared such that the amount obtained by multiplying the amount of the probe by the length of base chains is multiplied by 0.5 to 3. The distance between the solid phase and each nozzle of the inkjet head is defined to almost 0.2 to 0.5 mm, so that a spot of about 170 to 250 µm in diameter can be formed on the solid phase when the probe medium is discharged from the nozzle of the inkjet head (the discharge amount is about 20 picoliter). In addition, any spot due to splashing at the time of discharging the liquid from the nozzle (hereinafter, referred to as "satellite spot") is not observed at all by a visual observation using a loupe.

Here, for example, for improving the detection accuracy (spot integration intensity) at the time of detecting a target substance or the like using the probe-immobilized substrate, after immobilizing the probe on the surface of the solid phase, the non-probe-bonding portion of the substrate may be blocked so as not to bind to the target substance or the like in a sample. For example, the blocking is performed by immersing the substrate in an aqueous solution of 2% bovine serum albumin (BSA) for about two hours at room temperature. Considering the effect of preventing the target substance from adsorbing to a portion of the substrate other than the probe-immobilized portion, the BSA aqueous solution is suitable. Note that, the blocking process may be performed as needs arise. For example, the supply of a sample to the probe-immobilized substrate is limited to each spot, so that the blocking may not be performed when substantially no adhesion of the sample on a portion other than the spot is observed. The adhesion of the sample to the portion other than the spot varies depending on the material of the substrate. In particular, when the substrate is made of glass, quartz, or silica-coated resin, the blocking process may not be performed.

The probe-immobilized substrate prepared in this way may be constructed to, for example, include a plurality of spots each having the same probe depending on the applications thereof. Alternatively, it may be constructed to include a plurality of spots respectively having different types of probes. The type, amount, and array of the probes can be properly changed if necessary. The probe-immobilized substrate on which the probes are arranged in this way at high density is prepared. Then, such a substrate is used for the detection of a target substance, the identification of the base sequence of the target substance, or the like. For example, when the substrate is used for the detection of a single-stranded nucleic acid as a target substance having a known base sequence which may be contained in a sample, a single-stranded nucleic acid having a base sequence complementary to the base sequence of the single-stranded nucleic acid of the target substance is used as a probe. A probe-immobilized substrate, on which a plurality of spots including the probe are arranged on the solid phase thereof, is prepared. Then, a sample is supplied to each spot of the probe-immobilized substrate, followed by placing the substrate under the conditions in which the single-stranded nucleic acids of the target substance and the probe are hybridized. After that, the presence or absence of the hybrid at each spot is detected by the known method such as fluorescent detection. Thus, the presence or absence of the target substance in the sample can be detected.

When it is used for identifying the base sequence of a single-stranded nucleic acids provided as a target substance in a sample, two or more candidates of the base sequence of the single-stranded nucleic acids of the target substance are set and then the single-stranded nucleic acids having a base sequence complementary to each of those base sequences are spotted as a probe on the substrate. Next, the sample is supplied to each spot and then placed under the conditions of allowing the hybridization between the single-stranded nucleic acids of the target substance and the probe. After that, the presence or absence of the hybrid at each spot is detected by the known method such as fluorescent detection. Consequently, a base sequence can be identified with respect to the single-stranded nucleic acids of the target substance. In addition, other applications of the probe-immobilized substrate of the present invention may be, for example, applications for screening a specific base sequence to be recognized by a DNA-binding protein or screening a chemical substance having the property of binding to DNA.

The probe medium may be provided as one containing a liquid medium including an organic solvent, a probe, a probe-soluble solvent, a probe-insoluble organic solvent, and a substance for solubilizing the probe in the organic solvent, and as a component to be added if required, an organic solvent for immobilizing the probe on the substrate. Those components may be divided into at least two groups of the components and then placed in different vessels so as to be prepared independently. They may be provided as a reagent kit such that the components in different vessels are mixed together in use.

For placing the probe in the vessel, preferably, the vessel can be sealed for preventing the contamination of other impurities or the like. Furthermore, it is required that the vessel can be opened for easily mixing at the time of immobilization. However, the opening of the vessel is not specifically limited and the probe kept in the vessel may be in the form of a solution or in the form of powders although it is not specifically limited. When the functional group is a mercapto group, or the like, considering the stability of the probe, the probe is pulverized by a freeze-drying method or the like and then stored without an increase in temperature. Even if the functional group is an amino group or the like, as a storage condition, it is preferable to keep the probe in a freezer for ensuring the stability of the probe. However, it is possible to change the storage condition depending on the storage period, probe types, probe functional groups, and so on. In this way, the probe may be kept in a vessel and it may be then mixed at the time of immobilizing on the substrate while being kept in the vessel.

In this application, when a surfactant is used as a substance for solubilizing the probe in an organic solvent, the surfactant is preferably in the form of a solution. However, the surfactant is not limited to this. It may be in the form of powdery solid matter as far as it can be dissolved in the solvent when in use.

For placing the probe-soluble solvent, the probe-insoluble organic solvent, and the organic solvent for immobilizing the probe on the substrate in the vessel, the vessel can be airtightly closed so as to prevent contamination of other impurities or the like and to prevent volatile loss of the solvent. Alternatively, the vessel is preferably a sealed vessel. In addition, it is preferably designed to be easily opened so as to simplify the mixing at the time of immobilization. However, the opening of the vessel is not specifically limited. In addition, the state of the solvent placed in the vessel is also not specifically limited, so that it may be in the form of a solution or solid matter. Furthermore, the organic solvent for immobilizing the probe on the substrate may be a solution hydrolyzed for the formation of a silanol group which is one of the functional groups used for the immobilization of the probe on the substrate. For the storage conditions, it is preferable to keep the solvent at room temperature for ensuring the stability of the solvent. However, it is possible to change the storage conditions according to the storage time or the like. In particular, if the hydrolyzed solution is used, it is preferable to avoid the temperature rise during the storage. In addition, it is preferable to obtain stability by adjusting pH at the time of hydrolysis and after the hydrolysis depending on the functional group of the organic solvent for immobilizing the probe on the substrate.

At the time of immobilizing the probe on the substrate, for mixing the probe and the organic solvent for immobilizing the probe, which are kept in the vessel, water or other solution may be added if required. In addition, a solvent such as water, which is a substance for sufficiently mixing them together to provide a probe medium, may be-kept in another vessel and mixed at the time of preparing the probe medium.

EXAMPLES

Hereinafter, the present invention will be described in more detail based on the examples.

Example 1

(1) Probe Synthesis

As a probe capable of specifically binding to a target substance, a single-stranded DNA probe was used. The single-stranded DNA probe having SEQ ID NO: 1 was synthesized using an automated DNA synthesizer (Model 380A, manufactured by Applied Biosystems, Co., Ltd.). On the end of the single-stranded DNA probe of SEQ ID NO: 1, a 18-mer oligomer having a hydroxyl group on its 5'-end bound to an amino acid group through a phosphate group and hexamethylene was prepared and used in the following experiments.

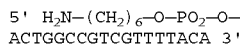
```
5' H2N-(CH2)6-O-PO2-O-
ACTGGCCGTCGTTTTACA 3'          SEQ ID NO: 1
```

(2) Probe Solvent

As a probe-soluble medium, water was used.

(3) Substance for Solubilizing Probe

As a substance for solubilizing a probe in an organic solvent, cetyltrimethyl ammonium bromide (n-hexadecyltrimethyl ammonium bromide) was used. For preparing an aqueous solution in which cetyltrimethylammonium bromide was completely dissolved, cetyltrimethylammonium bromide was dissolved while heating in a water bath at 50° C.

(4) Probe-Insoluble Solvent

As a probe-insoluble organic solvent, a silane coupling agent (trade name: KBE-9007, manufactured by Shin-Etsu Chemical Co., Ltd.) containing a silane compound (3-isocyanate propyltriethoxy silane) having an isocyanate group, isopropyl alcohol, and dipropylene glycol were used in the following experiments.

(5) Preparation of Probe Medium

The single-stranded DNA probe of SEQ ID NO: 1 described in the above item (1) was dispensed into 18-nmol aliquots and then dried up. Subsequently, 20 µl of pure water was dropped into each aliquot. 20 µl of an aqueous solution of about 65 mmol/l cetyltrimethyl ammonium bromide as a substance for solubilizing a probe in an organic solvent was dropped and mixed into a probe aqueous solution in which the probe was dissolved. Consequently, the DNA probe was precipitated in an aqueous solution, resulting in a white turbid probe medium. After centrifuging the DNA probe to be precipitated, 30 µl of the above-mentioned probe-immobilizing substance was dropped thereinto. After the mixture was sufficiently stirred and mixed, the mixture was left standing for 30 minutes.

Then, 500 µl of dipropylene glycol and 1,000 µl of isopropyl alcohol as organic solvents were dropped into the mixture and the mixture was stirred for 5 minutes.

Furthermore, polyvinyl alcohol (PVA) as a water-soluble polymer material was dissolved in pure water in a concentration of 0.5% by mass. For completely dissolving the PVA, it was heated at 80° C. in a hot bath while stirring for 60 minutes. After confirming that no material remained undissolved, the filtration was carried out for preventing the nozzles from clogging at the time of spotting to prepare the PVA aqueous solution.

Into the probe solution prepared as described above, 50 µl of the PVA aqueous solution prepared as described above was dropped. Finally, pure water was dropped thereinto to add up to 2 ml in the total amount of the probe medium and then the mixture was mixed by stirring for 5 minutes. After mixing, the mixture was left alone for 30 minutes, preparing a probe medium.

(6) Substrate Cleaning

A silica-coated soda lime glass substrate of 1×3 inches in size (about 1.1 mm in thickness) was rinsed with pure water to remove foreign matters from the surface of the substrate. Then, the substrate was treated for five minutes using a UV/$O_3$ cleaning apparatus to remove organic materials attached on the surface of the substrate. Subsequently, the substrate cleaned with UV/$O_3$ was placed in a cassette and immersed into an aqueous solution of 5% by volume of an inorganic alkali detergent (trade name: Semiclean KG, manufactured by Yokohama Oils & Fats Industry Co., Ltd.) while it was subjected to an ultrasonic wave irradiation for five minutes. Subsequently, the substrate and the cassette were rinsed in the flow of pure water and then washed well with water to remove the detergent attached on the glass substrate and the cassette. After rinsed well, the glass substrate was immersed in pure water together with the cassette and then cleaned by an ultrasonic wave for five minutes. After cleaned with the ultrasonic wave, the substrate and the cassette were rinsed in the flow of pure water to remove particles attached thereon. After washed with water, the glass substrate and the cassette were subjected to spin-drying. For confirming that the substrate was cleaned, the contract angle of pure water on the substrate was measured. As a result, all portions of the substrate were in a spread state.

(7) Spotting of Probe Medium

The probe medium prepared in the above item (5) was spotted on the substrate by using an inkjet apparatus. In this case, a piezo-jet head was used as an inkjet head of the apparatus. The piezo-jet head was filled with the probe medium and then the medium was spotted on a glass substrate prepared in the above item (6). Here, the distance between a liquid-discharging surface of the piezo-jet head and a liquid-attached surface of the glass substrate was about 0.5 mm. After the completion of the spotting, the glass substrate was observed using a microscope. As a result, it was confirmed that a spot array was formed in a matrix form on the surface of the glass substrate. The glass substrate after spotting was left standing on a hot plate heated at 80° C. for five minutes. The substrate treated on the hot plate was kept in a desiccator. Consequently, a probe-immobilized substrate (probe array) was prepared.

(8) Hybridization Process

A single-stranded DNA probe having a base sequence complementary to the single-stranded DNA probe of SEQ ID NO: 1 of the above item (1) was synthesized by the automated DNA synthesizer. Then, the 5'-end of the DNA probe was bound to rhodamine to obtain a labeled single-stranded DNA probe. Subsequently, the labeled single-stranded DNA probe was dissolved in a 1 M NaCl/50 mM phosphate buffer (pH 7.0) so as to have a final concentration of 50 nM. In this solution, the probe-immobilized substrate obtained in the above item (7) was immersed and then subjected to a hybridization process at room temperature (45° C.) for two hours. After that, the probe array was cleaned with the 1 M NaCl/50 mM phosphate buffer (pH 7.0), followed by washing out the single-stranded DNA probe which was not hybridized with the nucleic acids of the probe. Furthermore, after the excess salt content was removed with pure water, the probe array was dried with nitrogen blowing. Then, the fluorescence at the spot of the probe array was evaluated for its intensity with a fluorescent scanner (trade name: Gene Pix 4000B, manufactured by Axon Instruments, Inc.). For the evaluation, the power of a laser was set to 100% and PMT was set to 400 V.

(9) Results

The evaluation results of the fluorescent scanner in the above item (8) were analyzed. In the spot of the DNA probe of SEQ ID NO: 1, which was completely matched with the labeled single-stranded DNA probe, the brightness of the portion having a high fluorescence intensity at 532 nm was 5531. The fluorescence intensity integration value of the spot at 532 nm was 6593912. In addition, the fluorescence intensity of a portion other than the spot portion of the DNA probe was observed and the result was about 40. As a result of observing the spot of each DNA probe with fluorescence, the shape of each spot is almost a circle and substantially no difference in fluorescence intensity between spots obtained by spotting the same probe medium was observed. Furthermore, the distance between the adjacent spots is almost constant. It was observed that spots were arranged in a lattice form at intervals of about 300 µm.

Example 2

(1) Probe Synthesis

A single-stranded DNA probe was prepared just in the same manner as that of Example 1, and then used in the following experiments.

(2) Probe Solvent

Just in the same manner as that of Example 1, as a probe-soluble medium, water was used.

(3) Substance for Solubilizing Probe

As a substance for solubilizing a probe in an organic solvent, cetyltrimethyl ammonium chloride (n-hexadecyltrimethyl ammonium chloride) was used. For preparing an aqueous solution in which cetyltrimethylammonium chloride was completely dissolved, cetyltrimethylammonium chloride was dissolved while heating in a water bath at 50° C.

(4) Probe-Insoluble Solvent

Just in the same manner as that of Example 1, as a probe-insoluble organic solvent, an isocyanate silane coupling agent, isopropyl alcohol, and dipropylene glycol were prepared and used in the following experiments.

(5) Preparation of Probe Medium

The single-stranded DNA probe of SEQ ID NO: 1 was dispensed into 18-nmol aliquots and then dried up. Subsequently, 20 μl of pure water was dropped into each aliquot to dissolve it. 20 μl of an aqueous solution of about 163 mmol/l cetyltrimethyl ammonium chloride as a substance for solubilizing a probe in an organic solvent was dropped and mixed into the probe aqueous solution in which the probe was dissolved. Consequently, the DNA probe was precipitated in an aqueous solution, resulting in a white turbid probe medium. After centrifuging the DNA probe, 30 μl of the above-mentioned probe-immobilizing substance was dropped thereinto. After the mixture was sufficiently stirred and mixed, the mixture was left standing for 60 minutes.

Then, 500 μl of dipropylene glycol and 1,000 μl of isopropyl alcohol as organic solvents were dropped into the mixture and the mixture was mixed by stirring for 5 minutes.

Furthermore, just in the same manner as that of Example 1, the PVA solution was prepared. Into the probe solution prepared as described above, 50 μl of the PVA aqueous solution prepared as described above was dropped. Finally, pure water was dropped thereinto to add up to 2 ml in the total amount of the probe medium and then the mixture was mixed by stirring for 5 minutes. After mixing, the mixture was left alone for 30 minutes to prepare a probe medium.

(6) Substrate Cleaning

A glass substrate was prepared by cleaning the substrate just in the same manner as that of Example 1.

(7) Spotting of Probe Medium

Using the probe medium prepared in the above item (5), the probe medium was spotted in the same manner as that of Example 1 to prepare a probe-immobilized substrate. After the completion of the spotting, the glass substrate was examined under a microscope. It was observed that a spot array was formed in a matrix form on the surface of the glass substrate. The glass substrate after spotting was left standing on a hot plate heated at 80° C. for five minutes. The substrate treated on the hot plate was kept in a desiccator. Consequently, a probe-immobilized substrate (probe array) was prepared.

(8) Hybridization Process

Just in the same manner as that of Example 1, a hybridization process was conducted. After that, the probe array was cleaned with the 1 M NaCl/50 mM phosphate buffer (pH 7.0), followed by washing out the single-stranded DNA probe which was not hybridized with the nucleic acids of the probe. Furthermore, after the excess salt content was removed with pure water, the probe array was dried with nitrogen blowing. Then, the fluorescence at the spot of the probe array was evaluated for its intensity with a fluorescent scanner (trade name: Gene Pix 4000B, manufactured by Axon Instruments, Inc.). For the evaluation, the power of a laser was set to 100% and PMT was set to 400 V.

(9) Results

The evaluation results of the fluorescent scanner in the above item (8) were analyzed. In the spot of the DNA probe of SEQ ID NO: 1, which was completely matched with the labeled single-stranded DNA probe, the brightness of the portion having a high fluorescence intensity at 532 nm was 5836. The fluorescence intensity integration value of the spot at 532 nm was 6377211. In addition, the fluorescence intensity of a portion other than the spot portion of the DNA probe was observed and the result was about 50. As a result of observing the spot of each DNA probe with fluorescence, the shape of each spot is almost a circle and substantially no difference in fluorescence intensity between spots obtained by spotting the same probe medium was observed. Furthermore, the distance between the adjacent spots is almost constant. It was observed that spots were arranged in a lattice form at intervals of about 300 μm.

Example 3

(1) Probe Synthesis

A single-stranded DNA probe was prepared just in the same manner as that of Example 1, and then used in the following experiments.

(2) Probe Solvent

Just in the same manner as that of Example 1, as a probe-soluble medium, water was used.

(3) Substance for Solubilizing Probe

As a substance for making a probe soluble in an organic solvent, cetylpyridinium chloride was used. For preparing an aqueous solution in which cetylpyridinium chloride was completely dissolved, cetylpyridinium chloride was dissolved in water while being well stirred.

(4) Probe-Insoluble Solvent

As a probe-insoluble organic solvent, a silane coupling agent (trade name: Y-5187, manufactured by Nippon Unicar Company Ltd.) containing a silane compound (γ-isocyanate propyltrimethoxy silane) having an isocyanate group, isopropyl alcohol, and dipropylene glycol were used in the following experiments.

(5) Preparation of Probe Medium

The single-stranded DNA probe of SEQ ID NO: 1 described in the above item (1) of Example 1 was dispensed into 18-nmol aliquots and then dried up. Subsequently, 20 μl of pure water was dropped as the probe solvent into each aliquot to dissolve the probe therein. The mixture was well stirred such that no probe remained undissolved to precipitate a solution thereof to the bottom of the vessel by the centrifugation. Into the probe solution in which the probe was dissolved, 5 μl of an aqueous solution of about 65 mmol/l cetylpyridinium chloride as a substance for solbilizing a probe in an organic solvent was dropped and mixed. Consequently, the DNA probe was precipitated in an aqueous solution, resulting in a white turbid probe medium. After centrifuging the DNA probe to precipitate and separate from the solution, 5 μl of silane coupling agent among the above-mentioned probe-insoluble solvents was only dropped thereinto. After the mixture was gently mixed by stirring, the mixture was left standing for 60 minutes.

Then, 500 μl of dipropylene glycol and 1,000 μl of isopropyl alcohol as organic solvents were dropped into the mixture, and the mixture was mixed by stirring for 5 minutes.

Furthermore, polyvinyl alcohol (PVA) as a water-soluble polymer material was dissolved in pure water so as to have a concentration of 0.5% by mass. For completely dissolving the PVA, it was heated at 80° C. in a hot bath while stirring for 60 minutes. After confirming that no material remained undissolved, the filtration was carried out for preventing the nozzles from clogging at the time of spotting to prepare the PVA aqueous solution.

In the probe solution prepared as described above, 50 µl of the PVA aqueous solution prepared as described above was dropped. Finally, pure water was dropped into the mixture to add up to 2 ml in the total amount of the probe medium and the mixture was mixed by stirring for 5 minutes. After mixing, the mixture was left alone for 30 minutes to prepare a probe medium.

(6) Substrate Cleaning

A silica-coated soda lime glass substrate of 1×3 inches in size (about 1.1 mm in thickness) was rinsed with pure water to remove foreign matters from the surface of the substrate. Then, the substrate was treated for five minutes by using a UV/$O_3$ cleaning apparatus to remove organic materials attached on the surface of the substrate. Subsequently, the substrate cleaned with UV/$O_3$ was placed in a cassette and immersed into an aqueous solution of 5% by volume of an inorganic alkali detergent (trade name: Semiclean KG, manufactured by Yokohama Oils & Fats Industry Co., Ltd.) while it was subjected to an ultrasonic wave irradiation for five minutes. Subsequently, the substrate and the cassette were rinsed in the flow of pure water and then washed well with water to remove the detergent attached on the glass substrate and the cassette. After rinsed well, the glass substrate was immersed in pure water together with the cassette and then cleaned by an ultrasonic wave for five minutes. After cleaned with the ultrasonic wave, the substrate and the cassette were rinsed in the flow of pure water and washed with water to remove particles attached thereon. After washed with water, the glass substrate and the cassette were subjected to spin-drying. For confirming that the substrate was cleaned, the contract angle of pure water on the substrate was measured. As a result, all portions of the substrate were in a spread state.

(7) Spotting of Probe Medium

The probe medium prepared in the above item (5) was spotted on the substrate by using an inkjet apparatus. In this case, a piezo-jet head was used as an inkjet head of the apparatus. The piezo-jet head was filled with the probe medium and then the medium was spotted on a glass substrate prepared in the above item (5). Here, the distance between a liquid-discharging surface of the piezo-jet head and a liquid-attached surface of the glass substrate was about 0.5 mm. After the completion of the spotting, the glass substrate was observed with a loupe. As a result, it was confirmed that a spot array was formed in a matrix form on the surface of the glass substrate. The glass substrate after spotting was left standing on a hot plate heated at 80° C. for five minutes. The substrate treated on the hot plate was kept in a desiccator. Consequently, a probe-immobilized substrate (probe array) was prepared.

(8) Hybridization Process

A single-stranded DNA probe having a base sequence complementary to the single-stranded DNA probe of SEQ ID NO: 1 of the above item (1) was synthesized by the automated DNA synthesizer. Then, the 5'-end of the DNA probe was bound to rhodamine to obtain a labeled single-stranded DNA probe. Subsequently, the labeled single-stranded DNA probe was dissolved in a 1 M NaCl/50 mM phosphate buffer (pH 7.0) so as to have a final concentration of 50 nM. In this solution, the probe-immobilized substrate obtained in the above item (7) was immersed and then subjected to a hybridization process at room temperature (45° C.) for two hours. After that, the probe array was cleaned with the 1 M NaCl/50 mM phosphate buffer (pH 7.0), followed by washing out the single-stranded DNA probe which was not hybridized with the nucleic acids of the probe. Furthermore, after the excess salt content was removed with pure water, the probe array was dried with nitrogen blowing. Then, the fluorescence at the spot of the probe array was evaluated for its intensity with a fluorescent scanner (trade name: Gene Pix 4000B, manufactured by Axon Instruments, Inc.). For the evaluation, the power of a laser was set to 100% and PMT was set to 400 V.

(9) Results

The evaluation results of the fluorescent scanner in the above item (8) were analyzed. In the spot of the DNA probe of SEQ ID NO: 1, which was completely matched with the labeled single-stranded DNA probe, the brightness of the portion having a high fluorescence intensity at 532 nm was 22180. In addition, the fluorescence intensity of a portion other than the spot portion of the DNA probe was observed and the result was about 45. As a result of observing the spot of each DNA probe with fluorescence, the shape of each spot is almost a circle and substantially no difference in fluorescence intensity between spots obtained by spotting the same probe medium was observed. Furthermore, the distance between the adjacent spots was almost constant. It was observed that spots were arranged in a lattice form at intervals of about 300 µm.

Example 4

(1) Probe Synthesis

A single-stranded DNA probe was prepared just in the same manner as that of Example 1, and then used in the following experiments.

(2) Probe Solvent

Just in the same manner as that of Example 1, as a probe-soluble medium, water was used.

(3) Substance for Solubiliz Probe

Just in the same manner as that of Example 3, a solution in which a substance for making a probe soluble in an organic solvent was dissolved in pure water was prepared and used in the following experiments.

(4) Probe-Insoluble Solvent

Just in the same manner as that of Example 3, as a probe-insoluble organic solvent, a silane coupling agent containing a silane compound (γ-isocyanate propyltrimethoxy silane) having an isocyanate group, isopropyl alcohol, and dipropylene glycol were used in the following experiments.

(5) Preparation of Probe Medium

The single-stranded DNA probe of SEQ ID NO: 1 was dispensed into 18-nmol aliquots and then dried up. Subsequently, 20 µl of pure water was dropped into each aliquot to dissolve the probe in pure water. Into the probe aqueous solution in which the probe was dissolved, 10 µl of an aqueous solution of about 65 mmol/l cetylpyridinium chloride as a substance for solubilizing a probe in an organic solvent was dropped and mixed. Consequently, the DNA probe was precipitated in an aqueous solution, resulting in a white turbid probe medium. After centrifuging the DNA probe to be precipitated, 5 µl of only the silane coupling agent among the above-mentioned probe-insoluble solvents was dropped thereinto. After the mixture was sufficiently mixed by stirring, the mixture was left standing for 60 minutes.

Then, 500 µl of dipropylene glycol and 1,000 µl of isopropyl alcohol as organic solvents were dropped into the mixture, and the mixture was mixed by stirring for 5 minutes.

(6) Substrate Cleaning

Just in the same manner as that of Example 1, a glass substrate was prepared by cleaning the substrate.

(7) Spotting of Probe Medium

Using the probe medium prepared in the above item (5), the spotting of the probe medium was performed in the same manner as that of Example 1 to prepare a probe-immobilized substrate. After the completion of the spotting, the glass substrate was examined under a microscope. It was observed that a spot array was formed in a matrix form on the surface of the glass substrate. The glass substrate after spotting was left standing on a hot plate heated at 80° C. for five minutes. The substrate treated on the hot plate was kept in a desiccator. Consequently, a probe-immobilized substrate (probe array) was prepared.

(8) Hybridization Process

A hybridization process was performed just in the same manner as that of Example 1. After that, the probe array was cleaned with the 1 M NaCl/50 mM phosphate buffer (pH 7.0), followed by washing out the single-stranded DNA probe which was not hybridized with the nucleic acids of the probe. Furthermore, after the excess salt content was removed with pure water, the probe array was dried with nitrogen blowing. Then, the fluorescence at the spot of the probe array was evaluated for its intensity with a fluorescent scanner (trade name: Gene Pix 4000B, manufactured by Axon Instruments, Inc.). For the evaluation, the power of a laser was set to 100% and PMT was set to 400 V.

(9) Results

The evaluation results of the fluorescent scanner in the above item (8) were analyzed. In the spot of the DNA probe of SEQ ID NO: 1, which was completely matched with the labeled single-stranded DNA probe, the brightness of the portion having a high fluorescence intensity at 532 nm was 19570. In addition, the fluorescence intensity of a portion other than the spot portion of the DNA probe was observed and the result was about 45. As a result of observing the spot of each DNA probe with fluorescence, the shape of each spot is almost a circle and substantially no difference in fluorescence intensity between spots obtained by spotting the same probe medium was observed. Furthermore, the distance between the adjacent spots is almost constant. It was observed that spots were arranged in a lattice form at intervals of about 300 µm.

Example 5

(1) Probe Synthesis

A single-stranded DNA probe was prepared just as in the case of Example 1, and then used in the following experiments.

(2) Probe Solvent

Just in the same manner as that of Example 1, as a probe-soluble medium, water was used.

(3) Substance for Solubilizing Probe

Just in the same manner as that of Example 3, a solution in which a substance for solubilizing a probe in an organic solvent was dissolved in pure water was prepared and used in the following experiments.

(4) Probe-Insoluble Solvent

Just in the same manner as that of Example 3, as a probe-insoluble organic solvent, a silane coupling agent (trade name: Y-5187, manufactured by Nippon Unicar Company Ltd.) containing a silane compound (γ-isocyanate propyltrimethoxy silane) having an isocyanate group, isopropyl alcohol, and dipropylene glycol were used in the following experiments.

(5) Preparation of Probe Medium

The single-stranded DNA probe of SEQ ID NO: 1 was dispensed into 18-nmol aliquots and then dried up. Subsequently, 20 µl of pure water was dropped into each aliquot to dissolve the probe in pure water. Into the probe aqueous solution in which the probe was dissolved, 20 µl of an aqueous solution of about 65 mmol/l of cetylpyridinium chloride as a substance for solubilizing the probe in an organic solvent, was dropped and mixed. The probe medium was first clouded by mixing the substance for solubilizing the probe in the organic solvent thereinto. However, after dropping and mixing all of 20 µl of the solution, it was confirmed that the white turbidity gradually diminished and remained slightly. The DNA probe was precipitated by centrifugation. After the removal of a supernatant, among the probe-insoluble solvents, 5 µl of only the silane coupling agent was dropped thereinto. After the mixture was sufficiently mixed by stirring. After mixing, the resultant was left standing for 60 minutes.

Then, 500 µl of dipropylene glycol and 1,000 µl of isopropyl alcohol as organic solvents were dropped into the mixture and the mixture was mixed for 5 minutes.

Furthermore, just in the same manner as that of Example 1, the PVA solution was prepared. Into the probe solution prepared as described above, 50 µl of the PVA aqueous solution prepared as described above was dropped. Finally, pure water was dropped thereinto to add up to 2 ml in the total amount of the probe medium and then the mixture was mixed for 5 minutes. After mixing, the mixture was left alone for 30 minutes to prepare a probe medium.

(6) Substrate Cleaning

Just in the same manner as that of Example 1, a glass substrate was prepared by cleaning the substrate.

(7) Spotting of Probe Medium

Using the probe medium prepared in the above item (4), the spotting of the probe medium was performed in the same manner as that of Example 1 to prepare a probe-immobilized substrate. After the completion of the spotting, the glass substrate was examined under a microscope. It was observed that a spot array was formed in a matrix form on the surface of the glass substrate. The glass substrate after spotting was left standing on a hot plate heated at 80° C. for five minutes. The substrate treated on the hot plate was kept in a desiccator. Consequently, a probe-immobilized substrate (probe array) was prepared.

(8) Hybridization Process

Just in the same manner as that of Example 1, a hybridization process was conducted. After that, the probe array was cleaned with the 1 M NaCl/50 mM phosphate buffer (pH 7.0), followed by washing out the single-stranded DNA probe which was not hybridized with the nucleic acids of the probe. Furthermore, after the excess salt content was removed with pure water, the probe array was dried with nitrogen blowing. Then, the fluorescence at the spot of the probe array was evaluated for its intensity with a fluorescent scanner (trade name: Gene Pix 4000B, manufactured by Axon Instruments, Inc.). For the evaluation, the power of a laser was set to 100% and PMT was set to 400 V.

(9) Results

The evaluation results of the fluorescent scanner of the above item (8) were analyzed. In the spot of the DNA probe of SEQ ID NO: 1, which was completely matched with the labeled single-stranded DNA probe, the brightness of the portion having a high fluorescence intensity at 532 nm was 7322. In addition, the fluorescence intensity of a portion other than the spot portion of the DNA probe was observed and the result was about 45. As a result of observing the spot of each DNA probe with fluorescence, the shape of each spot is almost a circle. As compared with other examples, the outline of the spot was blurred and hardly recognized and the size of the spot was about ½. There was no difference in fluorescence intensity between the spots formed by spotting the same probe medium. Furthermore, it was observed that the distance between the adjacent spots was almost constant and the spots were arranged in a lattice form at intervals of about 300 μm.

Example 6

(1) Probe Synthesis

A single-stranded DNA probe was prepared just in the same manner as that of Example 1, and then used in the following experiments.

(2) Probe Solvent

Just in the same manner as that of Example 1, as a probe-soluble medium, water was used.

(3) Substance for Solubilzing Probe

Just in the same manner as that of Example 3, a solution in which a substance for solubilizing a probe in an organic solvent was dissolved in pure water was prepared and used in the following experiments.

(4) Probe-Insoluble Solvent

Just in the same manner as that of Example 3, as a probe-insoluble organic solvent, a silane coupling agent (trade name: Y-5187, manufactured by Nippon Unicar Company Ltd.) containing a silane compound (γ-isocyanate propyltrimethoxy silane) having an isocyanate group, isopropyl alcohol, and dipropylene glycol were used in the following experiments.

(5) Preparation of Probe Medium

The single-stranded DNA probe of SEQ ID NO: 1 was dispensed into 18-nmol aliquots and then dried up. Subsequently, 20 μl of pure water was dropped into each aliquot to dissolve it. Into the probe aqueous solution in which the probe was dissolved, 2.5 μl of an aqueous solution of about 65 mmol/l of cetylpyridinium chloride as a substance for solubilizing the probe in an organic solvent was dropped and mixed. The probe medium was slightly clouded by mixing the substance for solubilizing the probe in the organic solvent thereinto. The DNA probe was precipitated by centrifugation. After the removal of a supernatant, among the probe-insoluble solvents, 5 μl of only the silane coupling agent was dropped thereinto. After the mixture was sufficiently mixed by stirring. After mixing, it was left standing for 60 minutes.

Then, 500 μl of dipropylene glycol and 1,000 μl of isopropyl alcohol as organic solvents were dropped into the mixture was mixed by stirring for 5 minutes.

Furthermore, just as in the same manner as that of Example 1, the PVA solution was prepared. Into the probe solution prepared as described above, 50 μl of the PVA aqueous solution prepared as described above was dropped. Finally, pure water was dropped to add up to 2 ml in the total amount of the probe medium and then the mixture was mixed for 5 minutes. After mixing, the mixture was left alone for 30 minutes to prepare a probe medium.

(6) Substrate Cleaning

Just in the same manner as that of Example 1, a glass substrate was prepared by cleaning the substrate.

(7) Spotting of Probe Medium

Using the probe medium prepared in the above item (4), the spotting of the probe medium was performed in the manner way as that of Example 1 to prepare a probe-immobilized substrate. After the completion of the spotting, the glass substrate was examined under a microscope. It was observed that a spot array was formed in a matrix form on the surface of the glass substrate. The glass substrate after spotting was left standing on a hot plate heated at 80° C. for five minutes. The substrate treated on the hot plate was kept in a desiccator. Consequently, a probe-immobilized substrate (probe array) was prepared.

(8) Hybridization Process

Just in the same manner as that of Example 1, a hybridization process was conducted. After that, the probe array was cleaned with the 1 M NaCl/50 mM phosphate buffer (pH 7.0), followed by washing out the single-stranded DNA probe which was not hybridized with the nucleic acids of the probe. Furthermore, after the excess salt content was removed with pure water, the probe array was dried with nitrogen blowing. Then, the fluorescence at the spot of the probe array was evaluated for its intensity with a fluorescent scanner (trade name: Gene Pix 4000B, manufactured by Axon Instruments, Inc.). For the evaluation, the power of a laser was set to 100% and PMT was set to 400 V.

(9) Results

The evaluation results of the fluorescent scanner of the above item (8) were analyzed. In the spot of the DNA probe of SEQ ID NO: 1, which was completely matched with the labeled single-stranded DNA probe, the brightness of the portion having a high fluorescence intensity at 532 nm was 8976. In addition, the fluorescence intensity of a portion other than the spot portion of the DNA probe was observed and the result was about 45. As a result of observing the spot of each DNA probe with fluorescence, the shape of each spot is almost a circle. As compared with other examples, the outline of the spot was blurred and hardly recognized and the size of the spot was about ½. There was no difference in fluorescence intensity between the spots formed by spotting the same probe medium. Furthermore, it was observed that the distance between the adjacent spots was almost constant and the spots were arranged in a lattice shape at intervals of about 300 μm.

Comparative Example 1

(1) Probe Synthesis

A single-stranded DNA probe was prepared just in the same manner as that of Example 1, and then used in the following experiments.

(2) Substance for Solubilizing Probe

The substance for solubilizing the probe in the organic solvent, which was used in each of Examples 1 and 2, was not used in the following experiments.

(3) Probe-Immobilizing Substance

Just in the same manner as that of Example 1, an isocyanate silane coupling agent as a probe-immobilizing substance was prepared and then used in the following experiments.

(4) Preparation of Probe Medium

The single-stranded DNA probe of SEQ ID NO: 1 was dispensed into 18-nmol aliquots and then dried up. 20 μl of pure water was dropped thereinto to thereby dissolve it. Into a probe aqueous solution in which the probe was dissolved, 30 μl of the above-mentioned probe-immobilizing substance was dropped, and the mixture was sufficiently mixed by stirring. After mixing, it was left standing for 60 minutes.

Then, 500 μl of dipropylene glycol and 1,000 μl of isopropyl alcohol as organic solvents were dropped into the mixture and the mixture was mixed for 5 minutes.

Further, a PVA solution was prepared just in the same manner as that of Example 1. Into the probe solution prepared as described above, 50 μl of the PVA aqueous solution prepared as described above was dropped. Finally, pure water was dropped to add up to 2 ml in the total amount of the probe medium and then the mixture was mixed for 5 minutes. After mixing, the mixture was left alone for 30 minutes to prepare a probe medium.

(5) Substrate Cleaning

Just in the same manner as that of Example 1, a glass substrate was prepared by cleaning the substrate.

(6) Spotting of Probe Medium

Using the probe medium prepared in the above item (4), the spotting of the probe medium was performed in the same manner as that of Example 1 to prepare a probe-immobilized substrate. After the completion of the spotting, the glass substrate was examined under a microscope. It was observed that a spot array was formed in a matrix form on the surface of the glass substrate. The glass substrate after spotting was left standing on a hot plate heated at 80° C. for five minutes. The substrate treated on the hot plate was kept in a desiccator. Consequently, a probe-immobilized substrate (probe array) was prepared.

(7) Hybridization Process

A hybridization process was performed just in the same manner as that of Example 1. After that, the probe array was cleaned with the 1 M NaCl/50 mM phosphate buffer (pH 7.0), followed by washing out the single-stranded DNA probe which was not hybridized with the nucleic acids of the probe. Furthermore, after the excess salt content was removed with pure water, the probe array was dried with nitrogen blowing. Then, the fluorescence at the spot of the probe array was evaluated for its intensity with a fluorescent scanner (trade name: Gene Pix 4000B, manufactured by Axon Instruments, Inc.). For the evaluation, the power of a laser was set to 100% and PMT was set to 400 V.

(8) Results

The evaluation results of the fluorescent scanner of the above item (7) were analyzed. In the spot of the DNA probe of SEQ ID NO: 1, which was completely matched with the labeled single-stranded DNA probe, the brightness of the portion having a high fluorescence intensity at 532 nm was 5744. The fluorescence intensity integration value of the spot at 532 nm was 419192. In addition, the fluorescence intensity of a portion other than the spot portion of the DNA probe was observed and the result was about 40. As a result of observing the spot of each DNA probe with fluorescence, the shape of each spot is almost a circle. As compared with other examples, the size of the spot was reduced to about ¼. There was almost no difference in fluorescence intensity between the spots formed by spotting the same probe medium. Furthermore, it was observed that the distance between the adjacent spots was almost constant and the spots were arranged in a lattice form at intervals of about 300 μm.

What is claimed is:

1. A method of immobilizing a probe on a substrate, the probe being capable of specifically binding to a target substance, said method comprising the steps of:
    preparing a probe medium comprising (i) the probe, (ii) an organic solvent comprising a coupling agent for coupling the probe to the substrate, and (iii) a substance for solubilizing the probe in the organic solvent; and
    providing the probe medium on the substrate by spotting,
    wherein the coupling agent comprises silane, and
    wherein the substance for solubilizing the probe is a cationic surfactant.

2. The method according to claim 1, wherein the probe medium further comprises a solvent in which the probe is soluble.

3. The method according to claim 1, wherein an amount of the substance for solubilizing the probe in the organic solvent is adjusted within a range in which white turbidity of the probe medium can be observed.

* * * * *